United States Patent
Ninomiya et al.

(10) Patent No.: US 7,558,683 B2
(45) Date of Patent: *Jul. 7, 2009

(54) METHOD FOR INSPECTING DEFECT AND SYSTEM THEREFOR

(75) Inventors: Takanori Ninomiya, Hiratsuka (JP); Seiji Isogai, Hitachinaka (JP); Shigeru Matsui, Hitachinaka (JP); Toshiei Kurosaki, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/976,015

(22) Filed: Oct. 19, 2007

(65) Prior Publication Data

US 2008/0059083 A1 Mar. 6, 2008

Related U.S. Application Data

(63) Continuation of application No. 11/302,145, filed on Dec. 14, 2005, now Pat. No. 7,305,314, which is a continuation of application No. 10/888,021, filed on Jul. 12, 2004, now Pat. No. 7,010,447, which is a continuation of application No. 09/794,532, filed on Feb. 27, 2001, now Pat. No. 6,792,359.

(30) Foreign Application Priority Data

Jul. 26, 2000 (JP) ............................. 2000-231352

(51) Int. Cl.
*G01B 5/28* (2006.01)
*G06F 19/00* (2006.01)

(52) U.S. Cl. .......................................... 702/35; 702/84

(58) Field of Classification Search ................... 702/33, 702/35, 83, 84; 356/237.2, 237.3, 237.5; 250/306, 307, 310; 714/718, 799
See application file for complete search history.

(56) References Cited

U.S. PATENT DOCUMENTS

| | | | |
|---|---|---|---|
| 5,737,072 A | 4/1998 | Emery et al. | 356/73 |
| 5,801,965 A * | 9/1998 | Takagi et al. | 702/35 |
| 5,844,850 A | 12/1998 | Tsutsui et al. | 365/200 |
| 5,907,100 A | 5/1999 | Cook | 73/602 |
| 6,009,545 A | 12/1999 | Tsutsui et al. | 714/718 |
| 6,388,747 B2 | 5/2002 | Nara et al. | 356/394 |
| 6,476,913 B1 | 11/2002 | Machida et al. | 356/394 |
| 6,792,359 B2 | 9/2004 | Ninomiya et al. | 702/35 |

FOREIGN PATENT DOCUMENTS

JP          55-149829          11/1980

(Continued)

OTHER PUBLICATIONS

Masao Iri: *Calculation Geometry and Geometry Information Processing*, Kyoritsu Publishing Ltd., pp. 110-121, 1986.

*Primary Examiner*—Bryan Bui
(74) *Attorney, Agent, or Firm*—Kenyon & Kenyon LLP

(57) ABSTRACT

Based on a plurality of defects' position-coordinates and attribute detected by an inspecting apparatus, defects that are easily detectable by an observing apparatus are selected. With these selected defects employed as the indicator, the observing apparatus detects and observes the defects. Moreover, creating a coordinate transformation formula for representing a correlated relationship in the defects' position-coordinates between both the apparatuses, the observing apparatus transforms the defects' position-coordinates so as to observe the defects.

4 Claims, 9 Drawing Sheets

FOREIGN PATENT DOCUMENTS

| | | |
|---|---|---|
| JP | 59-157505 | 9/1984 |
| JP | 59-192943 | 11/1984 |
| JP | 59-232344 | 12/1984 |
| JP | 02-071377 | 3/1990 |
| JP | 02-100393 | 4/1990 |
| JP | 03-156947 | 7/1991 |
| JP | 04-027850 | 1/1992 |
| JP | 04-216904 | 8/1992 |
| JP | 06-162987 | 6/1994 |
| JP | 07-140085 | 6/1995 |
| JP | 09-022676 | 1/1997 |
| JP | 10-340935 | 12/1998 |
| JP | 11-167893 | 6/1999 |
| JP | 2002/39959 | 2/2002 |
| WO | WO97/35337 | 9/1997 |

* cited by examiner

METHOD FOR INSPECTING DEFECT AND SYSTEM THEREFOR

This is a continuation of application Ser. No. 11/302,145 filed 14 Dec. 2005, now U.S. Pat. No. 7,305,314 which is a continuation of application Ser. No 10/888,021 filed 12 Jul. 2004, U.S. Pat. No. 7,010,447, which is a continuation of application Ser. No. 09/794,532 filed 27 Feb. 2001, U.S. Pat. No. 6,792,359, which claims priority to Japanese Patent Application No. 2000-231352 filed 26 Jul. 2000, the contents of which are incorporated herein by reference.

BACKGROUND OF THE INVENTION

The present invention relates to a defect inspecting method and a defect inspecting system for the inspection of defects existing on a substrate. Here, examples of the substrate are a semiconductor wafer and a mask used for the fabrication of a semiconductor device.

An inspecting apparatus or the like allows the detection of the defects that exist on the substrate such as the semiconductor wafer and the mask. Moreover, the use of an observing apparatus allows observing the details of the defects, collecting the observed images thereof, and analyzing the defects. In the defect inspecting system like this, the observing apparatus is required to be able to promptly execute the positioning as to where the defects detected by the inspecting apparatus exist on the substrate.

Conventionally, as a method of observing the defects on the substrate, there has been known the following method: The substrate as a whole or a portion thereof is inspected in advance so as to confirm whether or not the defects exist. Then, the positions of the defects thus found are stored as their coordinates on the substrate. Next, these stored coordinates are inputted into the observing apparatus through a communications member or a storage medium. Finally, based on the coordinates, the position-alignment is performed so that the defects will enter an observing field-of-view of the observing apparatus, then executing the observation.

At this occasion, if it is the case where the inspecting apparatus and the observing apparatus co-use the same substrate holding mechanism and substrate displacing mechanism and where the substrate remains held by the substrate holding mechanism at the time of transition from the inspection to the observation, simply displacing the observing field-of-view to the specified position-coordinates is enough for the position-alignment toward the observing apparatus. Accordingly, it is quite easy to permit the defects to enter the field-of-view.

In many cases, however, the inspecting apparatus requested to have a high throughput and the observing apparatus requested to have a high observing resolution are different apparatuses. Consequently, the easy position-alignment in the observing apparatus as described above is a difficult task. This requires the sharing of the coordinate system on the substrate by the inspecting apparatus and the observing apparatus through the use of some kind of method. Thus, for example, the following processing is executed: Positions of predetermined plurality of points on the substrate are detected using the inspecting apparatus and the observing apparatus. Then, the coordinate systems characteristic of the respective apparatuses are corrected based on this detection result, thereby causing the substrate coordinate system to be shared by both of the apparatuses.

As the concrete method therefor, there have been known the following methods, for example: A method in which the plurality of points provided along the circumference of the substrate and becoming a criterion of the positioning are constrained mechanically by the substrate holding mechanism, or a method in which an image of a predetermined pattern existing beforehand on the substrate is detected and the coordinate systems are corrected based on the position of this pattern.

JP-A-3-156947 has disclosed one example of the methods in which there is used the coordinate system that is common to a plurality of apparatuses including the inspecting apparatus and the observing apparatus.

In the above-described prior art method of mechanically constraining the points on the substrate, there exists a problem in the mechanical position reproducibility, i.e., the dimension accuracy. For example, it is difficult to implement the high-accuracy position-alignment at a level of micrometers.

Also, concerning the above-described method of correcting the coordinate systems in accordance with the detected pattern position, the method is inapplicable to, for example, the substrate before the pattern's formation of course. Moreover, when, for example, the inspecting apparatus is an optical type and the observing apparatus is an electron-beam type, i.e., the pattern detecting methods and the pattern detecting accuracies are different between both of the apparatuses, there exists the case where it is impossible to detect the same pattern in common to the apparatuses. Accordingly, the method is inapplicable to this case.

For example, when the substrate is covered with a transparent oxide-film and a pattern existing under the oxide-film is used for the position-alignment of the optical type inspecting apparatus, it is difficult to detect the pattern with the use of the electron-beam type observing apparatus.

JP-A-11-167893 has disclosed one example of the methods of detecting foreign substances in the case where the detecting methods are different between the inspecting apparatus and the observing apparatus. In this example, using both the coordinate values of the foreign substances on the substrate and the coordinate values thereof on the stage, it is intended to implement the sharing of the coordinate system between the inspecting apparatus and the observing apparatus. This makes it easier for the observing apparatus to find out the foreign substances that have been detected by the inspecting apparatus. Furthermore, the detected foreign substances are automatically selected depending on the characteristics such as the size, thereby enhancing the reliability of a correcting formula for the sharing of the coordinate system.

However, even if the inspecting apparatus and the observing apparatus employ the detecting methods similar to each other, when, for example, trying to observe into what form the defects detected at the time of the inspection have changed after the inspected substrate had been subjected to several processing steps, the pattern turns out to exist under a film formed at the processing steps. Consequently, it becomes impossible to detect the same pattern.

SUMMARY OF THE INVENTION

It is an object of the present invention to implement efficiency-heightening and time-shortening of a defect observing operation, a defect image collecting operation, and a defect analyzing operation.

Also, it is another object of the present invention to allow a short-time and high-efficiency defect observation to be executed when the inspecting method and the observing method differ from each other.

Conventionally, when the substrate before the pattern's formation is inspected and observed, or when the inspecting apparatus and the observing apparatus are unable to detect the same pattern, it was difficult to cause the defects detected by the inspecting apparatus to enter the observing field-of-view of the observing apparatus with a high-accuracy. As the countermeasures against this, for example, the following attempts have been made: The defects are searched for in such a manner as to reduce the observing magnification of the observing apparatus to a lower magnification, or the operator searches for the defects with the high magnification left unchanged. In such operations, however, there existed a problem of taking so much labor and time.

Also, conventionally, when the optical conditions employed differ between the inspecting method and the observing method, it was not necessarily easy for the observing apparatus to observe the defect candidates that have been detected by the inspecting apparatus. As a result, there existed a problem of spending wasted time in changing the observing conditions or making a search around where the defects exist.

When the observing apparatus performs the observation, the collection of the observed images, and the defect analysis toward the defects detected by the inspecting apparatus, the present invention executes the position-alignment toward the detected defects with a high-accuracy. This allows the images to be detected at a time with a higher magnification, thereby implementing the efficiency-heightening and the time-shortening of the defect observing operation, the defect image collecting operation, and the defect analyzing operation.

Also, when the inspecting method and the observing method differ from each other, the present invention excludes, from the inspection result, a defect candidate the detection of which is impossible by the observing method, thereby making it possible to execute the short-time and high-efficiency defect observation.

According to the embodiments of the present invention, in addition to in-substrate coordinate system plurality of defects' position-coordinates detected and extracted by the inspecting apparatus, attribute of the defects is outputted. Here, examples of the attribute are as follows: The dimension, the type, the scattered light amount, local variation in the luminance, the profile configuration, and so on.

Next, based on the defects' position-coordinates and the defects' attribute inputted from the inspecting apparatus, a plurality of defects that are judged to be easily detectable by the observing apparatus are selected. Then, based on the selected defects' position-coordinates, the image detection is performed by the observing apparatus so as to find out the defects. Moreover, based on the defects' positions within the image, in-substrate coordinate system defects' position-coordinates defined on the observing apparatus side are calculated. Since, essentially, the substrate coordinate system is fixed onto the substrate, the in-substrate coordinate system represented defects' position-coordinates defined on the inspecting apparatus side and inputted from the inspecting apparatus should completely coincide with the in-substrate coordinate system defects' position-coordinates defined on the observing apparatus side.

As described earlier, however, the approximate position-alignment has been made where the mechanical position-alignment mechanism using, for example, the substrate circumference or the like makes it unhopeful to expect the high-accuracy. Consequently, it is usual at this point in time that the substrate coordinate system defined on the observing apparatus side differs from the substrate coordinate system defined on the inspecting apparatus side.

Accordingly, based on the in-substrate coordinate system defects' position-coordinates defined on the observing apparatus side and the in-substrate coordinate system defects' position-coordinates defined on the inspecting apparatus side and inputted from the inspecting apparatus, a coordinate transformation from the substrate coordinate system defined by the inspecting apparatus to the substrate coordinate system defined by the observing apparatus is derived with respect to the defects selected by the inspecting apparatus.

In accordance with this coordinate transformation, the defects' position-coordinates inputted from the inspecting apparatus are transformed into the position-coordinates in the substrate coordinate system defined by the observing apparatus. Hereinafter, the defect observation and the like will be executed based on these transformed position-coordinates.

Also, information on this coordinate transformation is saved and stored in a database with a set of the inspecting apparatus and the observing apparatus regarded as the unit. When executing the observation at the next opportunity, the position-alignment is performed first, using the information on this coordinate transformation. If a new coordinate transformation is derived by the above-described method, the above-described information on the coordinate transformation is updated.

In the present invention, the defects that actually exist on the substrate and are easily detectable in common by the observing apparatus are selected, then being used as the criterion of the substrate position-alignment. Consequently, even when there exists no pattern for the position-alignment, or even when, if any, the pattern is unable to be used in common to the inspecting apparatus and the observing apparatus, it becomes possible for the observing apparatus to execute the position-alignment toward the defects' positions with a high-accuracy.

Also, in the present invention, based on the defects' position-coordinates and the defects' attribute, only the defects that are judged to be easily detectable by the observing apparatus are observed. This makes the efficient defect observation possible.

Furthermore, the information on the coordinate transformation between the inspecting apparatus and the observing apparatus is stored in the database for use, or the information is updated. This makes it possible to always execute the defect observation based on a more precise positioning.

As described earlier, when the observing apparatus performs the observation, the collection of the observed images, and the defect analysis toward the defects detected by the inspecting apparatus, the present invention executes the position-alignment toward the detected defects with a high-accuracy. This allows the images to be detected at a time with a higher magnification, thereby making it possible to implement the efficiency-heightening and the time-shortening of the defect observing operation, the defect image collecting operation, and the defect analyzing operation.

Also, when the inspecting method and the observing method differ from each other, the present invention excludes, from the inspection result, a defect candidate the detection of which is impossible by the observing method, thereby making it possible to provide the method of executing the short-time and high-efficiency defect observation.

DETAILED DESCRIPTION OF THE EMBODIMENTS

Figure 1:
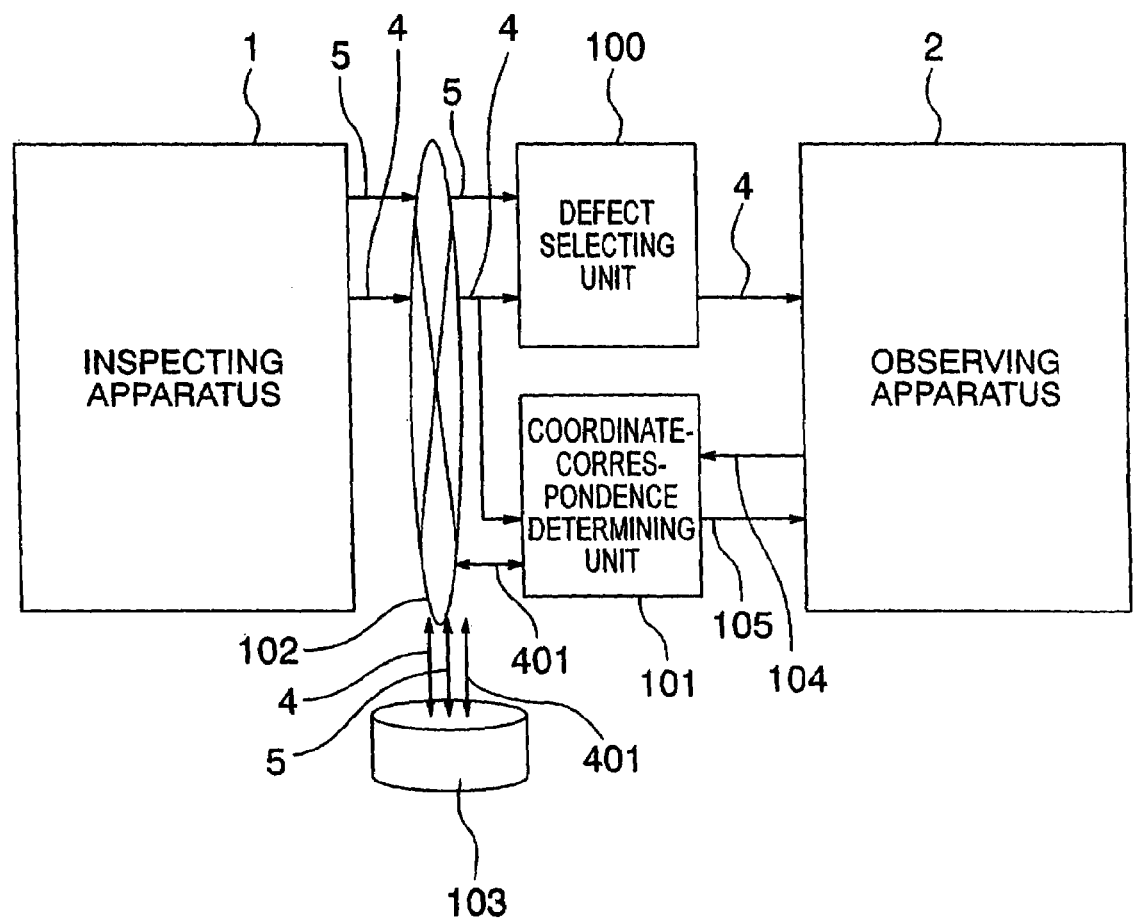
FIG. 1 is a conceptual diagram for illustrating the configuration of a defect inspecting system.

Referring to FIGS. 1 to 7, the explanation will be given below concerning the 1st embodiment of the present invention. FIG. 1 is a conceptual diagram for illustrating the configuration of a defect inspecting system.

In the present embodiment, the target to be inspected is a semiconductor wafer before a pattern's formation by etching. Using an inspecting apparatus 1 that is an optical type inspecting apparatus using the detection of scattered laser light, defects on the surface are inspected. Then, observing the defects is performed using an observing apparatus 2 that is a scanning type electron microscope. Although, in the present embodiment, foreign substances are considered as the example of the defects, the same concept as here also makes it possible to detect and observe pattern defects such as shorts or deficits in a circuit pattern.

Figure 2:
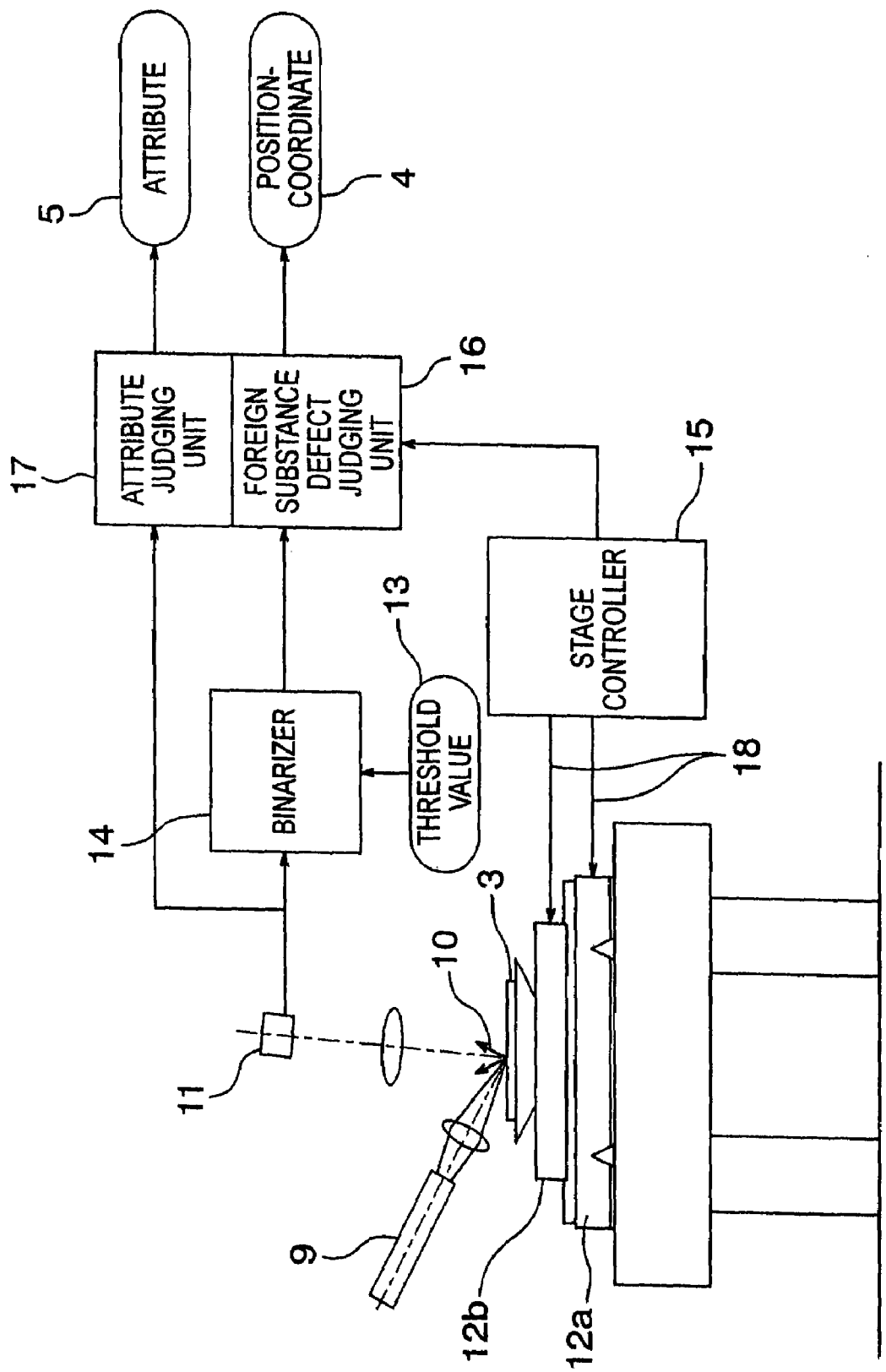
FIG. 2 is a side view for illustrating the configuration of a main portion of the inside of an inspecting apparatus.
Figure 3:
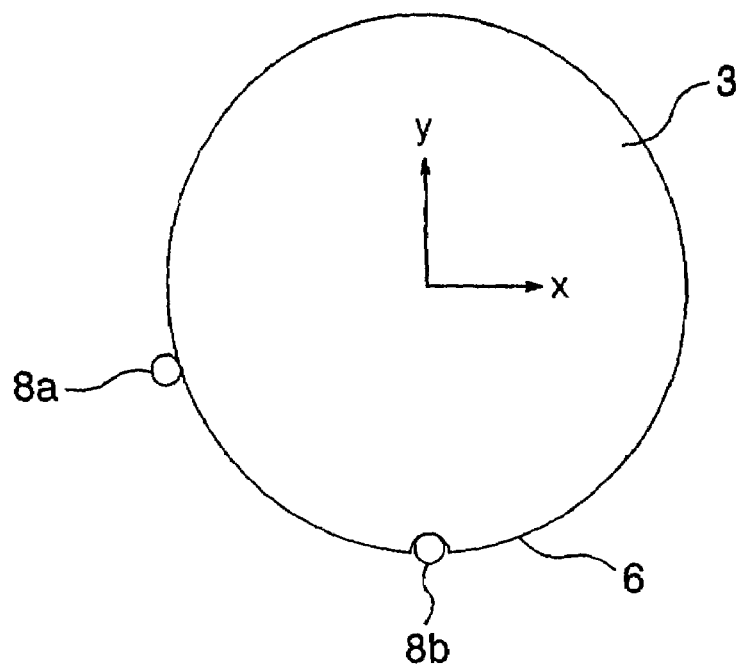
FIG. 3 is a plan view for illustrating an example of the state where a semiconductor wafer is installed on the inspecting apparatus.
Figure 4:
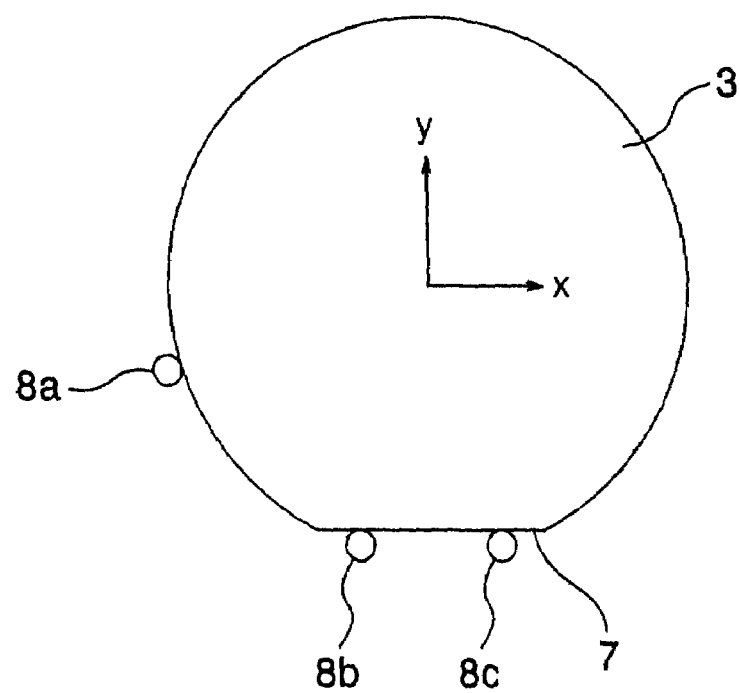
FIG. 4 is a plan view for illustrating an example of the state where the semiconductor wafer is installed on the inspecting apparatus.

FIG. 2 illustrates the configuration of a main portion of the inside of the inspecting apparatus 1 illustrated in FIG. 1. FIG. 3 is a plan view for illustrating an example of the state where a semiconductor wafer 3, i.e., the inspection target, is installed on the inspecting apparatus 1. FIG. 4 is a plan view for illustrating an example of the state where, similarly, the semiconductor wafer 3, i.e., the inspection target, is installed on the inspecting apparatus 1.

In the inspecting apparatus in FIG. 2, the irradiation with laser light is performed from an oblique direction by a laser 9, and the scattered laser light 10 is detected from above (or obliquely) by a detector 11. Displacing stages 12a, 12b allows a plurality of foreign substances to be detected all over the entire surface of the semiconductor wafer 3. The light amounts detected by the detector 11 are binarized by a binarizer 14. Then, binarized light amounts that exceed a predetermined threshold value 13 are regarded as the foreign substances, then being extracted as the defects.

In accordance with stage control information 18 from a stage controller 15, these defects' position-coordinates 4 in the coordinate system xy are outputted from a foreign substance defect judging unit 16. Moreover, at this time, the scattered light amounts are outputted together as attribute 5 of the defects by an attribute judging unit 17.

In this case, the coordinate system xy fixed onto the semiconductor wafer 3 can be determined mechanically by positioning pins 8a, 8b, 8c and so on that are provided in a unit such as a wafer holder on the stage 12b. This is performed using, as illustrated in FIG. 3, a notch 6, i.e., an incision portion of the semiconductor wafer 3, or using, as illustrated in FIG. 4, an orient flat in the straight line portion, i.e., an orifla 7. Also, concrete examples of the attribute 5 are the dimension, the type, the scattered light amount, and so on.

Figure 6:
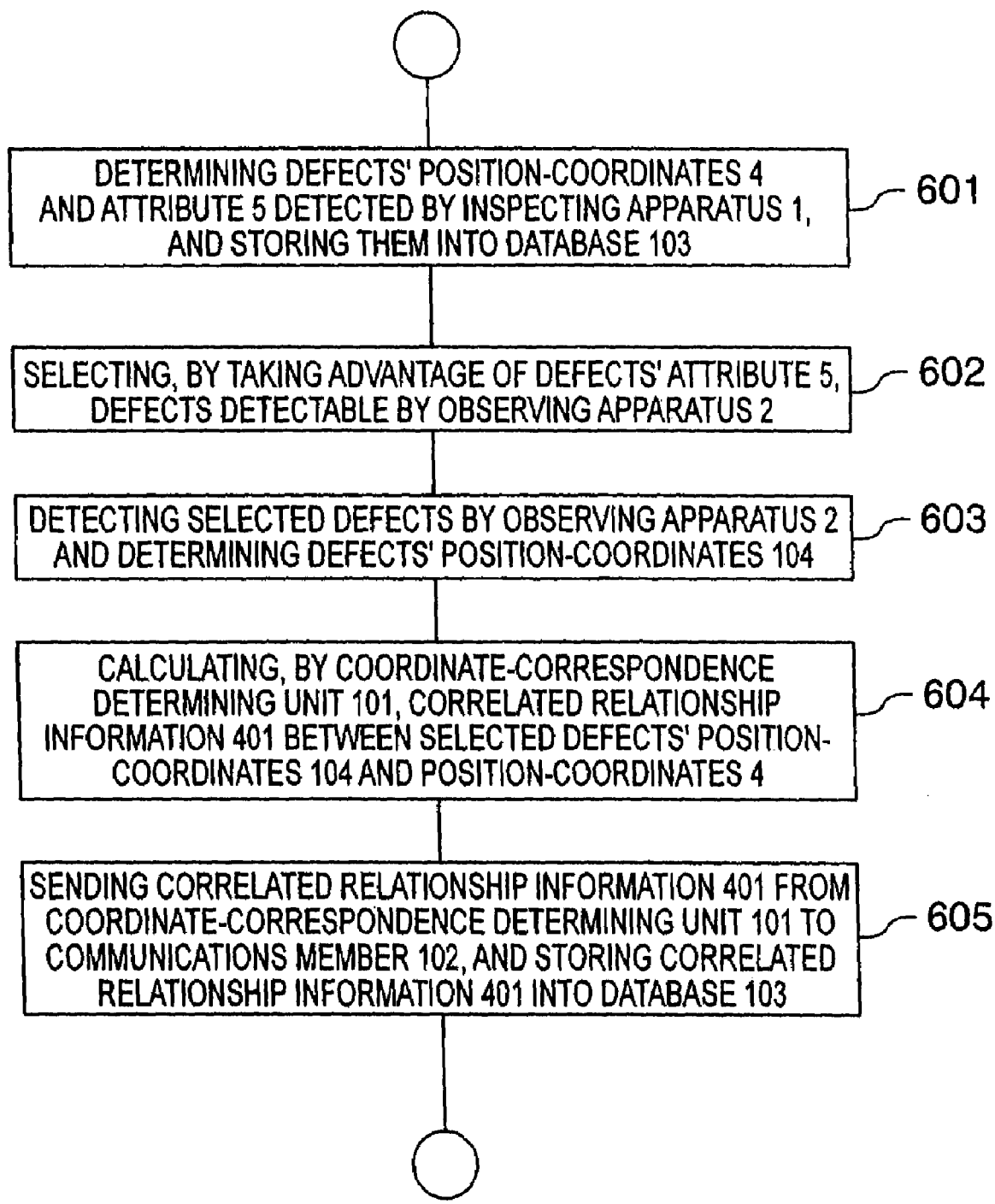
FIG. 6 is a flow chart for showing the procedure of an inspecting method.
Figure 7:
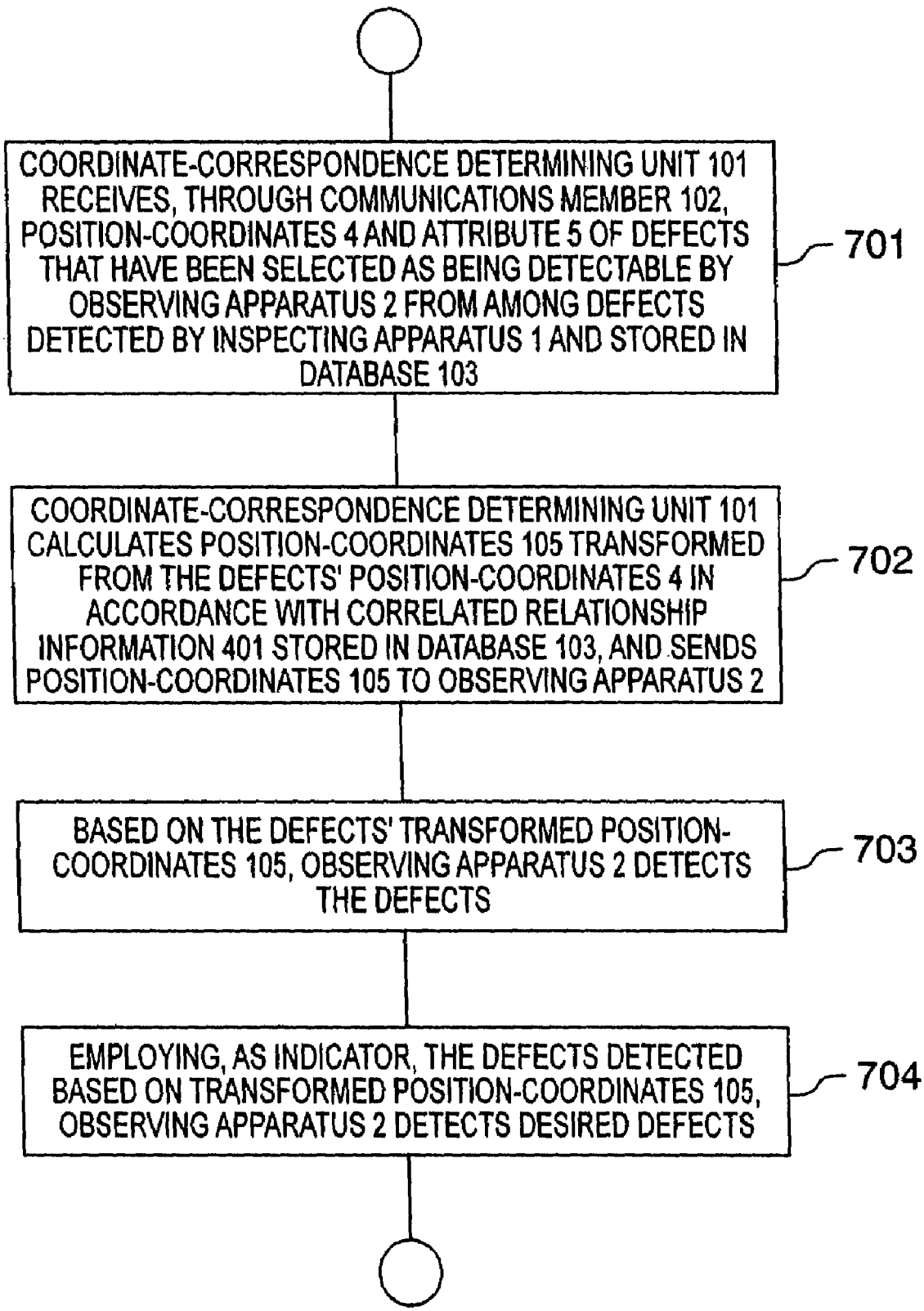
FIG. 7 is a flow chart for showing the procedure of an inspecting method.

Next, using the defects' position-coordinates 4 and the defects' attribute 5 obtained in this way, the position-alignment toward the defects at the time of observing the detects is performed. This is performed subsequently to the inspection of the defects. FIGS. 6, 7 are flow charts for showing the procedures of the inspecting method.

At a step 601 in FIG. 6 and in FIG. 1, the plurality of defects' position-coordinates 4 and the defects' attribute 5 are extracted or determined by the inspecting apparatus 1, then being once stored into a database 103 through a communications member 102 such as an area network, an intranet, and the Internet. The defects' position-coordinates 4 and the defects' attribute 5 are read out through the communications member 102 when necessary. Incidentally, they need not necessarily be read out through the communications member 102. Sending or receiving the information may also be performed using a storage medium such as a magnetic disk or an optical disk.

Next, at a step 602, from among the above-described defects and taking advantage of the defects' attribute 5, defects that are detectable by the observing apparatus 2 are selected. For example, taking advantage of the fact that there exists a certain correlated relationship between the scattered laser light amounts and the sizes of the foreign substances, i.e., the defects, a defect selecting unit 100 illustrated in FIG. 1 selects foreign substances the scattered light amounts of which are equivalent to a size within a certain fixed criterion that is detectable by the observing apparatus 2, i.e., for example a size in the rage of 1 µm to 3 µm. Next, at a step 603, the observing apparatus 2 detects the selected defects, thereby calculating their position-coordinates 104. Next, at a step 604, from the defects' position-coordinates 104 detected by the observing apparatus 2 and the defects' position-coordinates 4 extracted by the inspecting apparatus 1, a coordinate-correspondence determining unit 101 calculates information 401 on a correlated relationship between the coordinate systems in the detect observation.

At a step 605, together with a set of the respective identification numbers (or symbols) of the inspecting apparatus 1 and the observing apparatus 2, this correlated relationship information 401 is sent to the communications member 102, then being stored into the database 103. Every time observing a sample such as the substrate is performed, the correlated relationship information 401 is calculated in accordance with the same steps as those described above, and the correlated relationship information 401 stored in the database 103 is updated.

Incidentally, the database 103 into which the correlated relationship information 401 is stored may be directly connected to the coordinate-correspondence determining unit 101 without the linkage of the communications member 102. Also, in the above-described detect observation, if the correlated relationship information 401 between the coordinate systems has been already stored in the database 103, the defects' position-coordinates 4 from the inspecting apparatus 1 may be corrected using the information for their use at the time of the observation.

In this way, the above-described selection is executed using the attribute 5 of the defects that are assumed to be easily detectable. The selection may be performed by the inspecting apparatus 1. Also, using the defects' attribute 5 outputted from the inspecting apparatus 1, the selection may be performed by another apparatus. Moreover, fetching the defects' attribute 5 into the observing apparatus 2, the selection may be performed by the observing apparatus 2.

Next, using the correlated relationship information 401 stored in the database 103, the explanation will be given concerning a method of detecting a desired defect using the observing apparatus 2.

In FIG. 7, at a step 701, the coordinate-correspondence determining unit 101 receives, through the communications member 102, the position-coordinates 4 and the attribute 5 of the defects that have been selected as being detectable by the observing apparatus 2 from among the plurality of defects detected by the inspecting apparatus 1 and stored in the database 103 at the step 601 in FIG. 6. Next, at a step 702, the coordinate-correspondence determining unit 101 calculates position-coordinates 105 transformed from the defects' position-coordinates 4 in accordance with the correlated relationship information 401 stored in the database 103, then sending the transformed position-coordinates 105 to the observing apparatus 2. At a step 703, based on the above-described defects' transformed position-coordinates 105, the observing apparatus 2 detects the defects. Moreover, at a step 704, employing the detected defects as the indicator, the observing apparatus 2 detects and observes the desired defect wished to be observed in detail.

In the present embodiment, the above-described processings in the defect selecting unit 100 and the coordinate-correspondence determining unit 101 are set to be a mode carried out by a software system.

Figure 5:
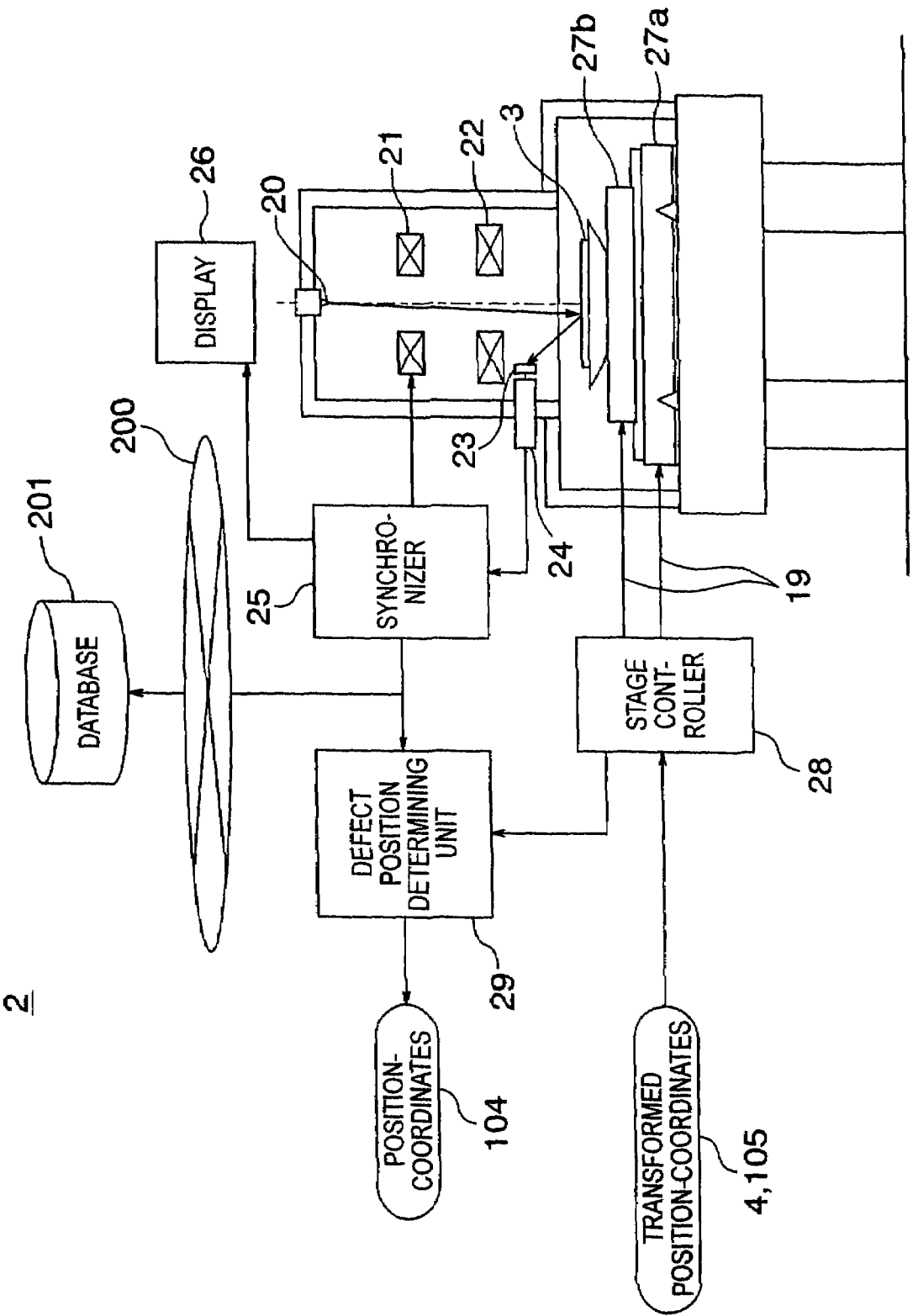
FIG. 5 is a side view for representing the configuration of a scanning type electron microscope, using the partially transverse cross section.

Next, the explanation will be given concerning an embodiment where the scanning type electron microscope is employed as the observing apparatus 2 in FIG. 1. FIG. 5 is a side view for representing the configuration of the scanning type electron microscope, i.e., the observing apparatus 2, using the partially transverse cross section.

An electron-beam emitted from an electron source 20 is deflected in the x, y directions by a deflector 21. When scanning the semiconductor wafer 3 using the electron-beam converged by a converging lens 22, secondary electrons are generated. Then, the secondary electrons are converted into an electrical signal by a detector including a scintillator 23 and a photomultiplier tube 24. Next, this electrical signal is outputted to a display 26, that is synchronized with the deflection of the electron-beam by a synchronizer 25, thereby obtaining a 2-dimensional electron-beam image. Changing the deflection width of the electron-beam makes it possible to easily change the magnification of the 2-dimensional electron-beam image.

A stage controller 28 sends, to a defect position determining unit 29, the defects' position-coordinates 4 sent from the defect selecting unit 100 in FIG. 1, the transformed position-coordinates 105 sent from the coordinate-correspondence determining unit 101, and stage control information 19 for controlling the positions of stages 27a, 27b.

The defect position determining unit 29 calculates the defects' position-coordinates 104 from the electron-beam' position information from the synchronizer 25 and the information from the stage controller 28, then sending the position-coordinates 104 to the coordinate-correspondence determining unit 101 in FIG. 1.

Also, the electrical signal detected by the detector including the scintillator 23 and the photomultiplier tube 24 is digitized using an AD converter (not illustrated). Then, using a communications member 200 such as an intranet or the Internet, the digitized signal is stored into a database 201 in a state of being related with the position-coordinates and so on. This makes it possible to save and reuse the image information.

Here, although there has been illustrated the embodiment where the database 201 is located outside the observing apparatus 2 and the information is transmitted using the communications member 200, the database 201 may be located inside the observing apparatus 2. Also, instead of using the database 201, the information may be stored in a storage medium such as a memory.

Concerning the positioning of the semiconductor wafer 3 in the observing apparatus 2, the following can be considered: The positioning by the mechanical method such as the one using the positioning pins illustrated in FIGS. 3, 4 as is the case with the inspecting apparatus 1, or in addition to this, the positioning by a method of observing a positioning mark so as to determine the coordinate system of the inspection target. In the present embodiment, since the semiconductor wafer before the pattern's formation is employed as the inspection target, no positioning mark has been formed. Accordingly, there has been used the positioning by the mechanical method such as the positioning pins.

The coordinate system determined here is the coordinate system that is characteristic of the inspection target. Thus, essentially the coordinate system is calculated in such a manner that it becomes identical to the coordinate system determined by the inspecting apparatus 1. In many cases, however, the positioning method in the observing apparatus 2 (in this case, positions of the positioning pins or the like) is not always the same as the positioning method in the inspecting apparatus 1. In addition, an error at the time of determining the coordinate system exists in both the inspecting apparatus 1 and the observing apparatus 2. As a result, the coordinate system determined by the observing apparatus 2 does not completely coincide with the coordinate system determined by the inspecting apparatus 1. Consequently, even if, using directly the defects' position-coordinates 4, i.e., the output from the inspecting apparatus 1, an attempt to detect the image is made by displacing the stages 27a, 27b of the scanning type electron microscope, i.e., the observing apparatus 2, and displacing the observing field-of-view, in many cases, the attempt proves to be unsuccessful in finding out the defects in the center of the observing field-of-view.

In view of this situation, at first, limiting the above-described defects to the defects selected by the defect selecting unit 100 illustrated in FIG. 1, detecting the defects' image is performed. As described earlier, the defects selected by the defect selecting unit 100 are the plurality of defects which are selected in accordance with the criterion of being easily detectable by the observing apparatus 2 and thus the size of which is equal to, for example, 1 μm or more. As a result, their existences can be confirmed easily even in a lower magnification of an order of guaranteeing that the defects securely enter the field-of-view, for example, a magnification of 5000 times or less. Also, since the upper limit of the selected defects' size has been defined, the defects never extend off the field-of-view. In this case, as a method of automatically recognizing the defects' positions from the detected image, there exists the method of recognizing the defects' positions from whether the luminance of the detected image is simply brighter or darker in comparison with the periphery thereof.

When the selected defects are unable to be detected by the observing apparatus 2 even if the above-described method is employed and executed, the defects are excluded from the selection. Also, if the relationship between the coordinate system determined by the inspecting apparatus 1 and the coordinate system determined by the observing apparatus 2 has been stored in advance in the database 103, by executing the coordinate transformation through the use of this relationship, the defects may be detected again.

In this way, concerning the defects selected as the one that should be detected first by the observing apparatus 2 from among the defects detected by the inspecting apparatus 1, there can be obtained a pair of the defects' position-coordinates 4 (x, y) in the inspection target coordinate system xy determined by the inspecting apparatus 1 and the defects' position-coordinates 104 (x', y') in the inspection 20 target coordinate system x'y' determined by the observing apparatus 2. Creating N sets of the pairs and using a coordinate group including these N sets of pairs $(x_i, y_i) (x'_i, y'_i)$ (i=1, 2, ..., N), the transformation formula from the coordinate system determined by the inspecting apparatus 1 to the coordinate system determined by the observing apparatus 2 is derived.

For example, designating, as formula 1, the transformation formula between the coordinate system xy determined by the inspecting apparatus 1 and the coordinate system x'y' determined by the observing apparatus 2, least-squares approximation method is employed. Thus, after partially differentiating $\epsilon^2$ defined by formula 2 by $a_{11}, a_{12}, a_{21}, a_{22}, x_0,$ and $y_0$, respectively, the obtained results are set to be =0 and solved. This allows the respective coefficients $a_{11}, a_{12}, a_{21}, a_{22}, x_0,$ and $y_0$ to be determined from two sets of three-solution simultaneous linear equations, i.e., formulae 3, 4.

$$x' = a_{11}x + a_{12}y + x_0 \quad \text{[formula 1]}$$
$$y' = a_{21}x + a_{22}y + y_0$$

$$\varepsilon^2 = \sum_i (\{X'_1 - (a_{11}x_i + a_{12}y_i + x_o)\}^2 + \quad \text{[formula 2]}$$
$$\{y'_i - (a_{21}x_i + a_{22}y_i + y_0)\}^2)$$

$$\begin{pmatrix} \sum_i x_i^2 & \sum_i x_i y_i & \sum_i x_i \\ \sum_i x_i y_i & \sum_i y_i^2 & \sum_i y_i \\ \sum_i x_i & \sum_i y_i & \sum_i 1 \end{pmatrix} \begin{pmatrix} a_{11} \\ a_{12} \\ x_0 \end{pmatrix} = \begin{pmatrix} \sum_i x'_i x_i \\ \sum_i x'_i y_i \\ \sum_i x'_i \end{pmatrix} \quad \text{[formula 3]}$$

$$\begin{pmatrix} \sum_i x_i^2 & \sum_i x_i y_i & \sum_i x_i \\ \sum_i x_i y_i & \sum_i y_i^2 & \sum_i y_i \\ \sum_i x_i & \sum_i y_i & \sum_i 1 \end{pmatrix} \begin{pmatrix} a_{21} \\ a_{22} \\ y_0 \end{pmatrix} = \begin{pmatrix} \sum_i y'_i x_i \\ \sum_i y'_i y_i \\ \sum_i y'_i \end{pmatrix} \quad \text{[formula 4]}$$

In this case, focusing the defects even further and selecting the defects so that the defects will distribute all over the entire surface of the inspection target uniformly, the detection by the observing apparatus 2 is performed. This makes it possible to enhance the transformation formula's accuracy and to shorten the image detecting time and the image calculating time.

Now, using the transformation formula determined in this way, as illustrated in FIG. 1, all the defects' position-coordinates 4 outputted from the inspecting apparatus 1 are transformed into the position-coordinates in the coordinate system determined by the observing apparatus 2. Taking advantage of the transformed position-coordinates 105, the position-alignment of the semiconductor wafer 3 toward the coordinates' positions is performed by the stages 27a, 27b. Then, the image detection is performed with the magnification enhanced up to, for example, 20000 times or more. This makes it possible to observe all the detected defects in detail or to record the detailed observed image.

According to the present embodiment of the present invention, even in the case of the semiconductor wafer before the pattern's formation, it becomes possible to execute the short-time and detailed observation of the foreign substances, the defects, or the like Observing the defects on the semiconductor wafer is executed using the defect inspecting method or the defect inspecting system as described above. This allows the cause of a defect occurrence to be discovered in the fabrication process of semiconductor devices in an early time, thereby making it possible to obtain the semiconductor devices with an excellent yield.

Next, referring to FIGS. 8 to 9, the explanation will be given below concerning the 2nd embodiment of the present invention. As is the case with FIG. 1, FIG. 8 is a conceptual diagram for illustrating the configuration of a defect inspecting system, and FIG. 9 is a side view for illustrating the configuration of a main portion of the inside of an optical type inspecting apparatus.

Although, in the present embodiment as well, a semiconductor wafer is employed as the inspection target, the semiconductor wafer is a pattern-formed wafer on which a pattern, such as a pattern by etching or a resist pattern, has been formed.

Figure 8:
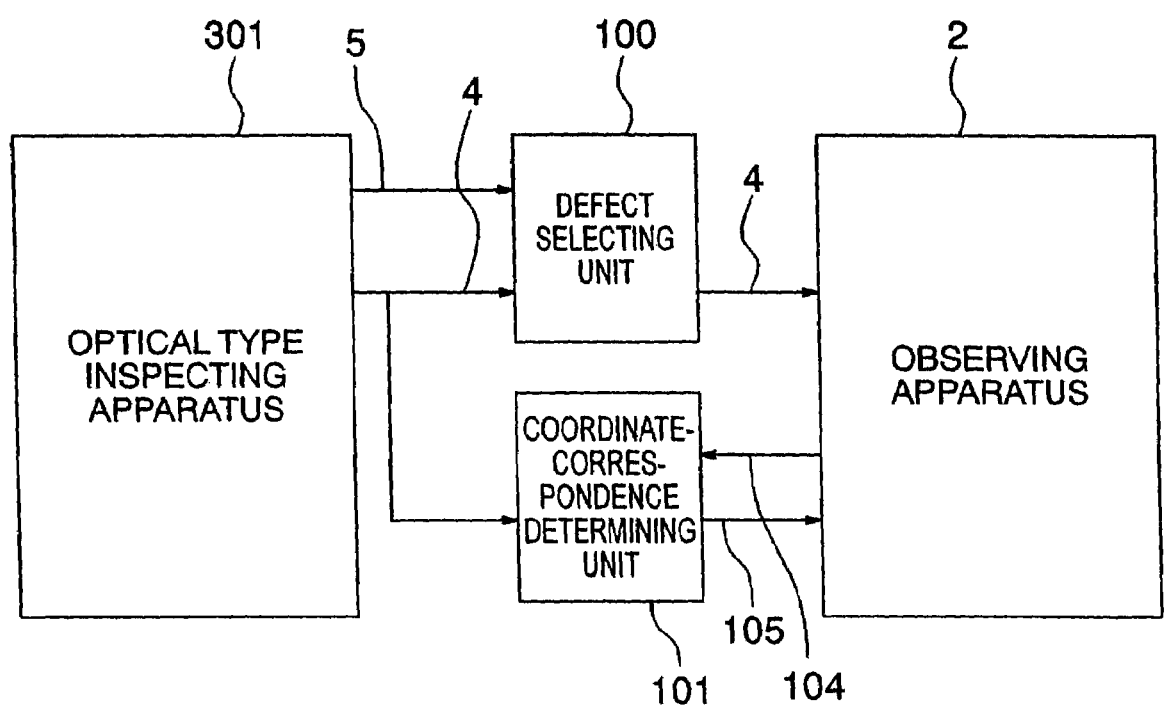
FIG. 8 is a conceptual diagram for illustrating the configuration of a defect inspecting system.

In the defect inspecting system illustrated in FIG. 8, using an optical type inspecting apparatus 301 using the image detection and the image comparison based on a bright field-of-view illumination, the detection is performed concerning pattern defects such as shorts or deficits formed on the semiconductor wafer, or foreign substances on the pattern surface. Then, observing the defects is performed using the scanning type electron microscope that is the observing apparatus 2.

Figure 9:
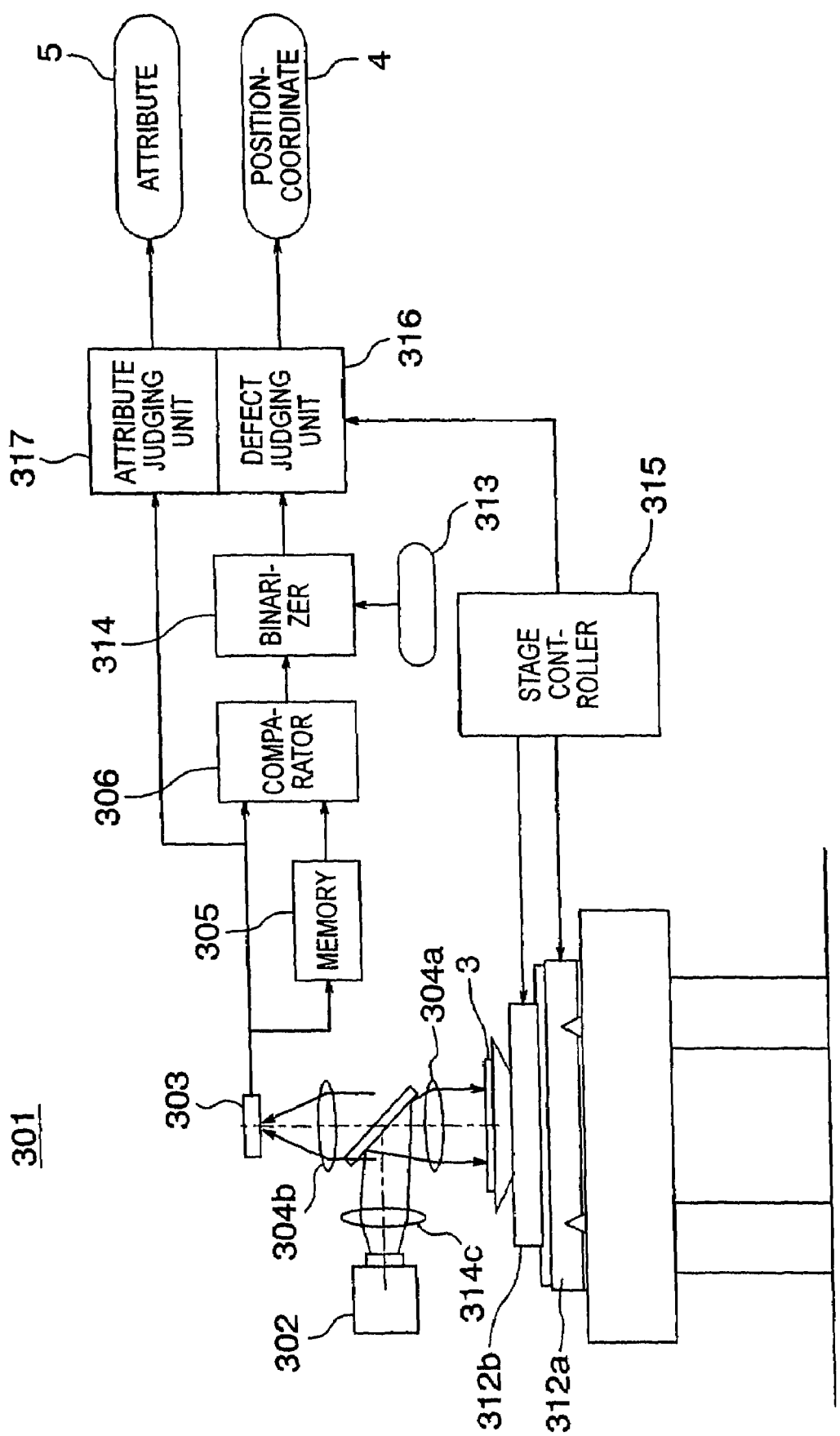
FIG. 9 is a side view for illustrating the configuration of a main portion of the inside of an optical type inspecting apparatus.

In FIG. 9, the semiconductor wafer 3 is inspected by the optical type inspecting apparatus 301. Then, the detected defects' position-coordinates 4 are outputted as the coordinates based on the coordinate system xy fixed onto the semiconductor wafer 3, i.e., the inspection target substrate. Also, the defects' attribute 5 detected with the defects' position-coordinates 4 are outputted together. In this case, as is the case with the coordinate systems illustrated in FIG. 3 or 4 and described in the 1st embodiment of the present invention, the coordinate system xy fixed onto the semiconductor wafer 3, after being determined mechanically by the positioning pins and so on using the notch 6 or the orifla 7 of the semiconductor wafer 3, is determined precisely by observing a positioning mark that is formed at a predetermined position and with a predetermined configuration on the semiconductor wafer 3.

In the optical type inspecting apparatus 301, as illustrated in FIG. 9, the irradiation with illuminating light is performed from an illuminating light source 302 onto the semiconductor wafer 3, using a lens 304a from above. Then, the reflected light is detected through a lens 304b by an image censor 303 positioned above. Displacing stages 312a, 312b allows the image to be detected all over the entire surface of the semiconductor wafer 3.

On the pattern-formed wafer 3, there exist repeated patterns the unit of which is equal to a light exposure unit at the time when the pattern is exposed to light or is equal to a value obtained by dividing the light exposure unit by an integer. Each repeated pattern exists for each die, or for each memory cell within a die. In the inspection, a delay quantity corresponding to a repeated spacing between these repeated patterns is created using a memory 305. Then, using a comparator 306, the delay quantity is compared with an image detected as a reference image. Next, the cases where the difference therebetween is judged to be larger than a certain fixed threshold value 313 by a binarizer 314 are detected as the defects. In addition, the defects' position-coordinates 4 in the coordinate system xy are caused to correspond to stage control information from a stage controller 315 and the defects' positions on the image, then being outputted from a defect judging unit 316. Moreover, the defects' attribute 5 is outputted together therewith by an attribute judging unit 317.

As a method of outputting the attribute of a detected defect, there exists a method of outputting the size of the defect as one attribute. In the above-described optical type inspecting apparatus 301, at the time of the image detection, the image detection is performed as an aggregation of the luminances of detecting units called pixels. Thus, for example, a defect detected as the non-coincidence between the repeated patterns by the image comparison can also be expressed by employing the pixel as the unit. Accordingly, the area can be expressed using the number of the pixels, and the dimension or the size thereof can also be expressed using the number of the pixels in the longitudinal, the transverse, or the longer-axis direction. Consequently, in the case of using the size of the defect as the defect's attribute, when the dimension within a fixed certain range, for example, a range of 0.7 μm to 2 μm, is employed as the criterion and the defects' positions included in this range are searched for by the image detection performed by the observing apparatus, the luminances and the number are detected in the pixel unit. As a result, even in a lower magnification, it becomes possible to find out the defect surely and without fail.

Also, as the defect's attribute other than the size, there can also be used, for example, local variation in the luminance of the detected defect portion. Namely, for example, the summation is taken concerning the difference between the maximum value and the minimum value in each portion of 2×2 pixels within the detected defect' region, and then the summation is normalized by being divided by the defect's size (i.e., the number of the pixels). This makes it possible to judge so-called "degree of roughness" of the defect. Also, as still another attribute, the square of the detected defect' profile length is divided by the area and, from to what extent the resultant value is large or small, it becomes possible to judge so-called "degree of serration" of the profile configuration. A defect with a large amount of the "degree of roughness" or the "degree of serration" is, in many cases, a defect exposed onto the surface of the inspection target. On account of this, utilizing the "degree of roughness" or the "degree of serration" makes it possible to judge whether the defect is positioned inside the inspection target or is exposed on the surface thereof.

In the present embodiment in particular, the scanning type electron microscope is employed as the observing apparatus 2. Accordingly, it is highly likely that the defect is unobservable unless exposed onto the surface, and thus these attributes are effective. The defect information from the optical type inspecting apparatus 301 is sieved and selected using the attributes, and only the defects that are observable by the scanning type electron microscope are extracted and observed, thereby allowing the observing time to be shortened.

Next, in FIG. 8, using the defects' position-coordinates 4 and the defects' attribute 5 obtained in this way, the position-alignment toward the defects in the defect observation is performed with a high-accuracy. This is performed subsequently to the inspection of the defects. In this case, the defects' position-coordinates 4 and the defects' attribute 5 are sent to the defect selecting unit 100 and the coordinate-correspondence determining unit 101, using a storage medium or a communications member such as an intranet or the Internet. Of course, database may be provided in the communications member, and sending or receiving the data may also be performed through the member.

At first, by the defect selecting unit 100, the defects, the sizes of which are included within the above-described certain fixed criterion and the "degree of roughness" and the "degree of serration" of which exceed a certain fixed criterion, are assumed to be easily detectable in the defect observation and are selected. Then, in the defect observation, the observing apparatus 2 detects the selected defects. Next, from the defects' position-coordinates 104 determined by the observing apparatus 2 and the defects' position-coordinates 4 by the inspecting apparatus 301, the coordinate-correspondence determining unit 101 determines a correlated relationship between the coordinate systems in the detect observation.

In this way, the above-described selection can be executed using the attribute of the defects that are assumed to be easily detectable. As is the case with the 1st embodiment, the selection may be performed by the inspecting apparatus 301, or may be performed by another apparatus using the attribute outputted from the inspecting apparatus 301. Moreover, fetching the attribute into the observing apparatus 2, the selection may be performed by the observing apparatus 2. In the present embodiment, the above-described processings are executed by a software system provided in the defect selecting unit 100 and the coordinate-correspondence determining unit 101 illustrated in FIG. 8.

In the present embodiment, the scanning type electron microscope employed as the observing apparatus 2 is of the same configuration and operation as those of the scanning type electron microscope in the 1st embodiment one example of which has been illustrated in FIG. 5.

In the observing apparatus 2 as well, as is the case with the optical type inspecting apparatus 301, the coordinate system of the inspection target is determined based on the positioning by the mechanical method such as the one using the positioning pins on the semiconductor wafer, or in addition to this, based on the method of observing a positioning mark or the like. In the present embodiment, the semiconductor wafer after the pattern's formation is employed as the inspection target. Accordingly, the positioning mark, which has been formed on the semiconductor wafer, can be used for determining the coordinate system of the inspection target.

At this time, there exists no problem if determining the coordinate system is possible using the same positioning mark as that used in the: optical type inspecting apparatus 301. If, however, this mark exists under an oxide-film insulating layer or the like and thus detecting the mark by an electron-beam is difficult, it turns out that another positioning mark that exists in the uppermost layer and is easy to detect will be used. Consequently, in this case, as is the case with the 1st embodiment, an error at the time of determining the coordinate system exists in both the optical type inspecting apparatus 301 and the observing apparatus 2. As a result, the coordinate system determined by the observing apparatus 2 does not completely coincide with the coordinate system determined by the optical type inspecting apparatus 301. On account of this, even if, using directly the defects' position-coordinates 4, i.e., the output from the optical type inspecting apparatus 301, an attempt to detect the image is made by displacing the stages 27a, 27b of the scanning type electron microscope, i.e., the observing apparatus 2, and displacing the observing field-of-view, in many cases, the attempt proves to be unsuccessful in finding out the defects in the center of the observing field-of-view.

In view of this situation, at first, limiting the defects to be detected to the defects selected by the defect selecting unit 100 using the above-described method, detecting the defects' image is performed. As described earlier, the selected defects are the ones the size of which is equal to, for example, 0.7 μm or more and which are selected with the image detecting easiness in the observing apparatus 2 employed as the criterion. As a result, their existences can be confirmed easily even in a lower magnification of an order of guaranteeing that the defects securely enter the field-of-view, for example, a magnification of 10000 times or less. Also, since the upper limit of the selected defects' size has been defined, the defects never extend off the field-of-view.

In this case, as a method of automatically recognizing the defects' positions from the detected image, as is the case with the optical type inspecting apparatus 301, the following methods are applicable: The method of performing the image comparison with the use of the patterns' repeated property, or the method of recognizing the defects' positions from whether the luminance of the detected image is simply brighter or darker in comparison with the periphery thereof.

When the selected defects are unable to be detected by the observing apparatus 2 even if the above-described method is employed and executed, the defects are excluded from the selection. The defects' position-coordinates 104 determined by the observing apparatus 2 are calculated in much the same way as the case in the 1st embodiment.

In this way, concerning the defects selected as the one that should be detected first by the observing apparatus 2 from among the defects detected by the optical type inspecting apparatus 301, there can be obtained a pair of the defects' position-coordinates 4 (x, y) in the inspection target coordinate system xy determined by the optical type inspecting apparatus 301 and the defects' position-coordinates 104 (x', y') in the inspection target coordinate system x'y' determined by the observing apparatus 2.

In much the same way as the case in the 1st embodiment, the transformation formula from the coordinate system xy determined by the optical type inspecting apparatus 301 to the coordinate system x'y' determined by the observing apparatus 2 is derived using a coordinate group including these N sets of pairs $(x_i, y_i)$ $(x'_i, y'_i)$ (i=1, 2, ..., N).

Now, using the transformation formula determined in this way, all the defects' position-coordinates 4 outputted from the optical type inspecting apparatus 301 are transformed into the position-coordinates in the coordinate system determined by the observing apparatus 2. Taking advantage of the transformed position-coordinates 105, the position-alignment of the semiconductor wafer 3 toward the coordinates' positions is performed by the stages 27a, 27b. Then, the image detection is performed with the magnification enhanced up to, for example, 30000 times or more. This makes it possible to observe all the detected defects in detail or to record the detailed observed image.

According to present invention, toward the semiconductor wafer after the pattern's formation, it becomes possible to execute the short-time and detailed observation of the defects, the foreign substances, or the like Observing the defects on the semiconductor wafer is executed using the defect inspecting method or the defect inspecting system as described above. This allows the cause of a defect occurrence to be discovered in the fabrication process of semiconductor devices in an early time, thereby making it possible to obtain the semiconductor devices with an excellent yield.

Figure 10:
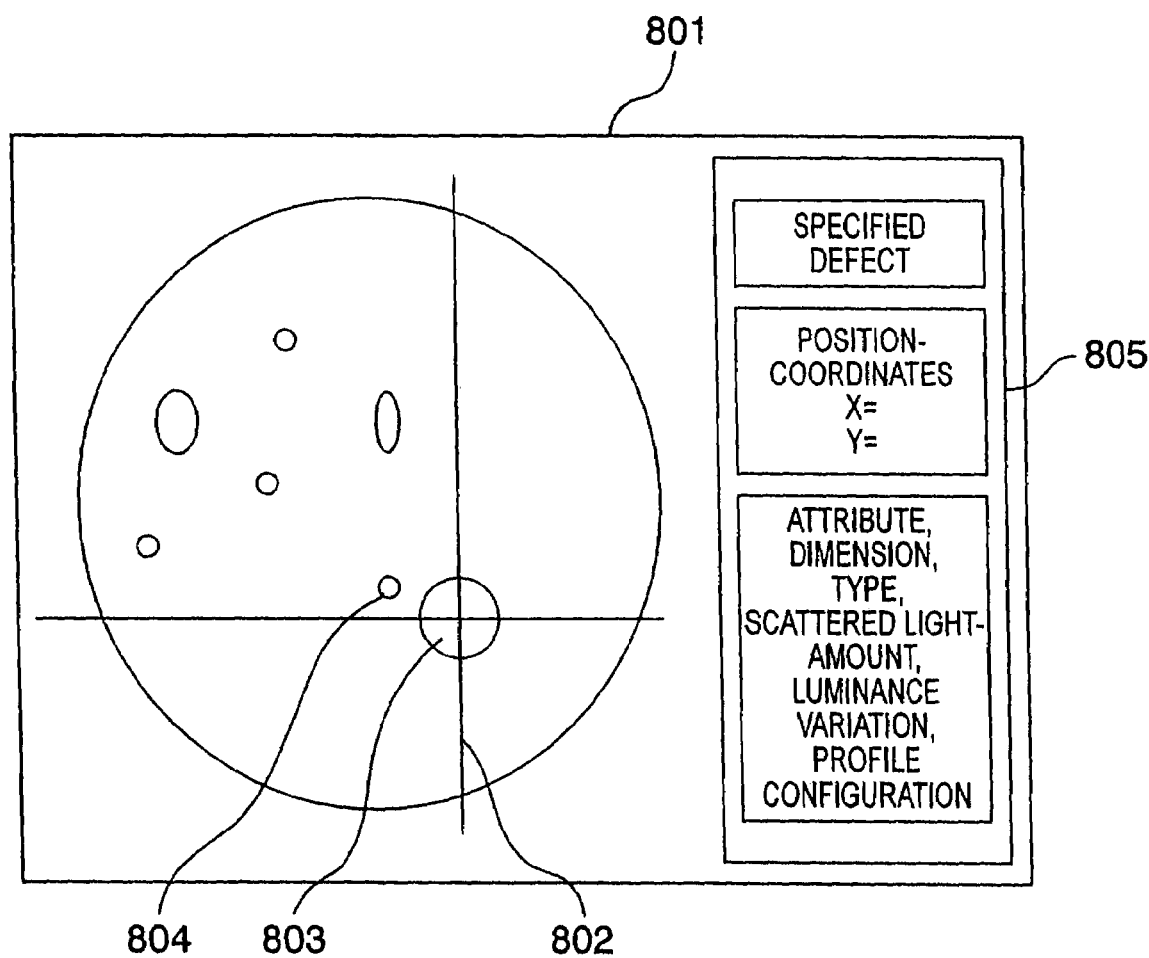
FIG. 10 is a screen diagram for illustrating an example of a screen display.

FIG. 10 is a screen diagram for illustrating an example of a screen display that is displayed on a monitor connected to the inspecting apparatus 1 illustrated in FIG. 2 or the optical type inspecting apparatus 301 illustrated in FIG. 9, or that is displayed on the display 26 of the observing apparatus 2 illustrated in FIG. 5.

On a screen 801, a plurality of defects detected by the inspecting apparatus 1 are displayed. Moreover, position-coordinates and attribute of a defect 803 specified by a cursor 802 are displayed in a specified defect displaying region 805. A defect 804 existing in proximity to the defect 803 is smaller in size than the defect 803, and thus it is difficult for the observing apparatus 2 to detect the defect 804. Meanwhile, the defect 803 is more detectable in many cases. Thus, taking advantage of one of the attribute of the defect 803 in proximity to the defect 804, i.e., its larger dimension in the present example, the observing apparatus 2 detects this defect 803 first. Once the defect 803 has been detected, the defect 804 wished to be found out is easy to detect, because the defect 804 exists in proximity to the defect 803.

Next, the explanation will be given below concerning the other modifications of the embodiments of the present invention.

As the examples of the inspecting apparatus 1, any publicly known method or apparatus may be used as long as it makes it possible to output the defects' position-coordinates. One example is the inspecting apparatus disclosed in JP-A-59-192943 where, employing the semiconductor wafer or the like as the target, the optical image is detected and the image comparison between the repeated patterns is performed utilizing the patterns' repeated property, and the non-coincidences therebetween are outputted as the defects.

Of course, not being limited to the semiconductor wafer, anything is allowable as the targets to be inspected. Such targets' examples are a mask for semiconductor, a printed board, a ceramic board, and so on all of which are before or after the pattern's formation. With respect to these targets, a lot of defect inspecting methods and systems have been known, the examples of which are disclosed in the following: JP-A-59-157505, JP-A-59-232344, JP-A-2-71377, JP-A-2-100393, JP-A-55-149829 JP-A-4-216904, and so on. In the present invention, any one of these inspecting apparatuses is allowable as long as it outputs the detected defects' position-coordinates.

Also, in addition to the above-described "size", "degree of roughness", and "degree of serration", the attribute of the defect assumed to be easily detectable by the characteristic of the observing apparatus can be used for the defect detection. As described earlier, the defect whose "degree of roughness", i.e., the local variation in the luminance, and whose "degree of serration", i.e., the profile configuration, exceed a certain fixed criterion is highly likely to be a defect exposed on the inspection target surface. Consequently, when performing the inspection optically and the observation by an electron-beam or an ion-beam, such a defect is highly likely to be detectable in common. As a result, only such defects are selected and observed, thereby allowing a wasted observing time to be eliminated.

JP-A-4-27850 has disclosed a publicly known example of a method of detecting an attribute other than the above-described attribute.

Also, as the defect observing method performed subsequently to the defect inspection, it is allowable to use any one of the publicly known image detecting methods or apparatuses preferable for observing the target defects, the examples of which are as follows: The optical image detecting method, the detecting method using the above-described electron-beam or ion-beam, the detecting method using a radiation, and so on. Concerning the detecting conditions, such as a detecting wavelength of the optical system and an accelerating voltage of the electron-beam or the ion-beam, it is also possible to select the optimum conditions for the observation.

In all the defects' observation, designating, as ΔX, ΔY, the differences between the defects' position-coordinates observed in sequence, the order of the observation is determined so that an amount obtained by summing up larger values out of the respective coordinate differences ΔX, ΔY becomes its minimum. This allows the observation to be executed in its minimum shortest time. Although it is not at all easy to determine this optimum solution, it is possible to obtain its approximate solution by taking advantage of a technique in "Calculation Geometry" and using the same method as a method of minimizing, for example, a pen displacing amount of a pen plotter. An example of such a technique is described in "Calculation Geometry and Geography Information Processing", Editorial Supervisor, Masao Iri, Kyouritu Publishing Ltd. pp. 110-121, published in 1986.

In the present invention, the defects that actually exist on the substrate and are easily detectable in common by the observing apparatus are selected, then being used as the criterion of the substrate position-alignment. Consequently, even when there exists no pattern for the position-alignment, or even when, if any, the pattern is unable to be used in common to the inspecting apparatus and the observing apparatus, it becomes possible for the observing apparatus to execute the position-alignment toward the defects' positions with a high-accuracy.

On account of this, in the cases as described above, when the observing apparatus performs the observation, the collection of the observed images, and the defect analysis toward the defects detected by the inspecting apparatus, the position-alignment toward the detected defects is executed with a high-accuracy. This allows the images to be detected at a time with a higher magnification, thereby resulting in an effect of being able to implement the efficiency-heightening and the time-shortening of the defect observing operation, the defect image collecting operation, and the defect analyzing operation.

Also, when the observing apparatus performs the observation, the collection of the observed images, and the defect analysis toward the defects detected by the inspecting apparatus, only the defects that are detectable by the observing apparatus are extracted in advance by taking advantage of the defects' attribute. This, similarly, results in an effect of being able to implement the efficiency-heightening and the time-shortening of the defect observing operation, the defect image collecting operation, and the defect analyzing operation.

As a result, it becomes possible to implement the time-shortening of the following operations: The observation and analysis of the foreign substances or crystalline defects on the semiconductor wafer before the pattern's formation, the observation and analysis of the defects or the foreign substances on the oxide film, the observation and analysis of the defects on the semiconductor wafer that has been subjected to a plurality of processing steps, and so on. Also, it becomes possible to automate the collection of these defects' or foreign substances' images.

What is claimed is:

1. A defect inspection system, comprising:
    a memory unit to store a correlated relationship between position-coordinates of defects defined by an inspecting apparatus and position-coordinates of defects defined by an observing apparatus, and defect coordinates and attributes detected by said inspecting apparatus, said attributes including detection capability;
    a defect selecting unit to select, from among defects detected by said inspecting apparatus that are in close proximity to a desired defect, defects as indicator defects including detection capability; and
    a coordinate-correspondence determining unit to obtain position-coordinates of said indicator defects to be detected by said observing apparatus based on said correlated relationship stored in said memory unit, wherein said observing apparatus detects said indicator defects based on obtained said position-coordinates by said coordinate-correspondence determining unit and detects said desired defect that is in close proximity of the indicator defects.

2. The defect inspection system according to claim 1, wherein:
    there are a plurality of indicator defects; and
    said observing apparatus detects said desired defect that is in close proximity of said indicator defects, at each detection of one indicator defect, and repeats at each of the plurality of indicator defects.

3. The defect inspection system according to claim 1, wherein:
    said correlated relationship between position-coordinates of defects defined by the inspecting apparatus and position-coordinates of defects defined by said observing apparatus is calculated using at least three sets of position-coordinates and employing a least-square approximation method.

4. The defect inspection system according to claim 1, wherein:
    said observing apparatus obtains an image of said desired defect in a magnification that is at least three times larger compared to when detecting indicator defects, and carrying out at least one of display, print or store said coordinates of said desired defect to memory.

* * * * *